(12) United States Patent
Haeuser et al.

(10) Patent No.: US 6,754,545 B2
(45) Date of Patent: Jun. 22, 2004

(54) METHOD FOR SYSTEMATICALLY ASSESSING THE QUALITY OF MEDICAL APPLIANCES THAT ARE IN OPERATION

(75) Inventors: Peter Haeuser, Effeltrich (DE); Werner Rosenberger, Altdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/085,062

(22) Filed: Mar. 1, 2002

(65) Prior Publication Data

US 2002/0123861 A1 Sep. 5, 2002

(30) Foreign Application Priority Data

Mar. 1, 2001 (DE) ......................................... 101 09 863

(51) Int. Cl.[7] ............................................. G06F 17/00
(52) U.S. Cl. ........................... 700/90; 707/7; 707/104.1
(58) Field of Search ................................. 700/108, 109, 700/110, 19, 20, 90; 707/104.1, 40, 7

(56) References Cited

U.S. PATENT DOCUMENTS 6,377,162 B1 * 4/2002 Delestienne et al. ... 340/286.07
2002/0082736 A1 * 6/2002 Lech et al. .................. 700/108

* cited by examiner

Primary Examiner—Leo Picard
Assistant Examiner—Carlos R. Ortiz
(74) Attorney, Agent, or Firm—Young & Thompson

(57) ABSTRACT

A method for systematically assessing the quality of medical appliances (11, 21, 31, 41) of a generic type that are in operation, in the case of which method data acquired during a regular inspection of the medical appliances (11, 21, 31, 41) are transmitted to a central database (51) and are evaluated by an evaluation device (52) assigned to the database (51).

13 Claims, 2 Drawing Sheets

METHOD FOR SYSTEMATICALLY
ASSESSING THE QUALITY OF MEDICAL
APPLIANCES THAT ARE IN OPERATION

BACKGROUND OF THE INVENTION

The invention relates to a method for systematically assessing the quality of medical appliances of a generic type that are in operation.

BRIEF DESCRITPION OF THE DRAWINGS

Manufacturers of medical appliances are generally interested in designing the appliances they manufacture to be of high quality in order to ensure trouble-free operation. In particular, systematic quality problems such as, for example, components of a defective charge that are used for a plurality of medical appliances, or underdimensioned modules, can lead to failures of a plurality of medical appliances. It is true that manufacturers assess individual protocols prepared, for example, by a service technician during maintenance or repair of a medical appliance. However, systematic quality problems can be identified only slowly and therefore unsatisfactorily with the aid of such a method.

Patent DE 41 37 742 A1 discloses a method for setting up a database in a spinning mill or a similar plant. Each time that maintenance work is carried out on spinning machines in the spinning mill, maintenance data determined on the basis of the maintenance work are recorded in a portable terminal and then transmitted to a processing computer. A database for the spinning machines is thereby set up automatically.

A monitoring system for presses having an electronic processor is disclosed in patent DE 197 49 002 A1. The monitoring system monitors functions and parameters of the press separately from the actual control of the press. A sensor connected to the processor measures the functions and parameters that are to be monitored. The processor subsequently processes signals measured by the sensor and transmits the processed signals to a remote unit via a communication network.

SUMMARY OF THE INVENTION

It is therefore the object of the invention to specify a method which permits preconditions for fast detection of systematic quality problems in medical appliances.

The object of the invention is achieved by means of a method for systematically assessing the quality of medical appliances of a generic type that are in operation, having the following method steps:

a) acquiring data that are generated during a regular inspection of the medical appliances at the site of the medical appliances, b) transmitting the data to a central database, c) assigning the transmitted data to modules in the medical appliances, and d) storing the data in collective files, assigned to the modules in the medical appliances, of the central database on the basis of the assignment to the modules in the medical appliance.

Thus, according to the invention data from medical appliances of a generic type are acquired during a regular inspection of the medical appliances. It is understood by generic type that the inspected medical appliances are appliances of the same, or at least a similar, type. In accordance with one embodiment of the invention, regular inspection can be, for example, a regular maintenance, a regular calibration measurement and/or a regular quality measurement. As a rule, medical appliances are required by statute to be maintained at regular intervals, for example, by a service technician, in order to avoid endangering persons examined with the aid of the medical appliances. Regular calibration measurements are carried out in the case of computer tomographs, for example, in order to ensure a high quality of the images produced with the aid of the computer tomographs. Quality measurements carried out regularly on magnetic resonance apparatuses fulfill a similar purpose. In this case, the data are acquired, for example, by the service technician during maintenance, or by an operator of the medical appliance in the course of the calibration or quality measurement. The data comprise, for example, information on the quality of an image produced with the aid of a medical appliance, data on a possibly altered adjustment of the medical appliance, defective modules that have therefore been replaced etc. These data are subsequently transmitted to the central database and evaluated by the evaluation device. Since the evaluation device evaluates not only the data of a medical appliance, but also data from a plurality of medical appliances of a generic type, systematic quality problems, that is to say quality problems that affect not only an individual medical appliance, but also many medical appliances of the generic type, can be identified quickly and reliably. Thereupon, on the basis of the evaluation the manufacturer can, for example, develop anew specifically specified modules in order to replace underdimensioned modules with the newly developed modules, or he can replace modules that comprise components of a defective charge by modules having high-quality components. A precondition for trouble-free operation of the medical appliances is thereby reliably set up.

The method according to the invention can be executed in a particularly practical fashion when, in accordance with one embodiment of the invention, the data are acquired by computers in the medical appliances, because there is then no need for the service technician to connect any external computer, for example a laptop, to the medical appliance while servicing it, or the quality or calibration measurement can be carried out automatically.

In a particularly preferred variant of the invention, it is provided that the data are transmitted with the aid of an information transmission network to which the medical appliances and the database can be connected. According to one variant of the invention, such an information transmission network can be a telephone network, the Internet, an Intranet or an Extranet. An Extranet is a network in the case of which at least parts of various Intranets are interconnected.

The method can be executed in a particularly timesaving and simple way when, according to a further embodiment of the invention, the computers of the medical appliances transmit the data to the database automatically.

In accordance with a further variant of the invention, the medical appliances are magnetic resonance apparatuses, computer tomographs, lithotripters, ultrasonic appliances or X-ray machines.

In order for a manufacturer, a marketing organization or a sales organization of the medical appliances to have a quick overview of the quality of medical appliances supplied, it is provided in accordance with a further variant of the invention that the database is assigned to a manufacturer, a marketing organization or a sales organization of the medical appliances.

BRIEF DESCRIPTION OF THE DRAWINGS

The method according to the invention is explained by way of example with the aid of the attached schematic drawings, in which.

DESCRIPTION OF THE PREFERRED EMBODIMENTS

Figure 1:
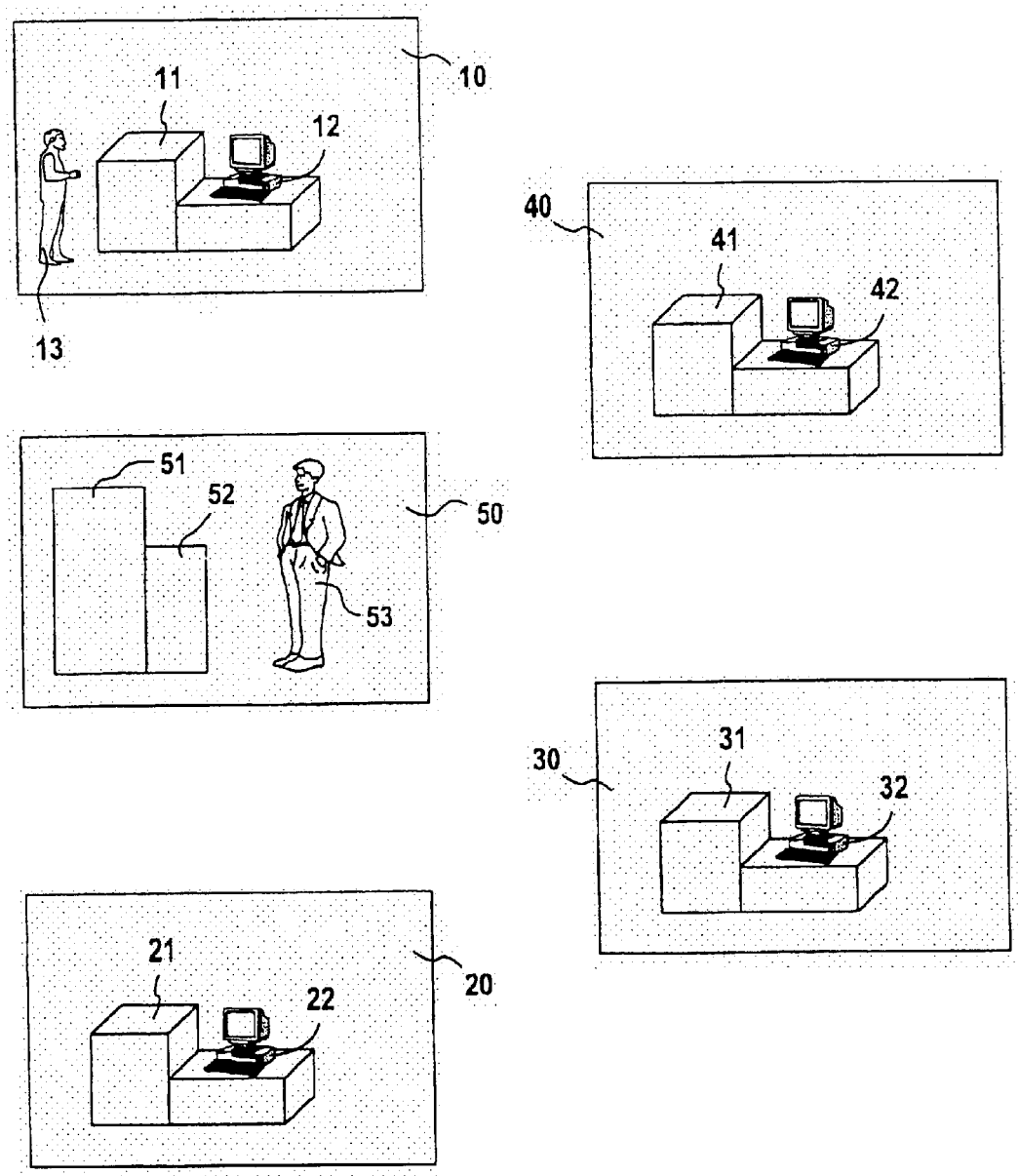
FIG. 1 shows a plurality of magnetic resonance apparatuses that are in operation.

FIG. 1 shows schematically by way of example four magnetic resonance apparatuses 11, 21, 31 and 41 of a plurality of magnetic resonance apparatuses of type A of a manufacturer 50 that are installed globally and are in operation. The magnetic resonance apparatuses 11, 21, 31 and 41 therefore belong to a generic type.

In the case of the present exemplary embodiment, the magnetic resonance apparatus 11 is located in a hospital 10, the magnetic resonance apparatus 21 in a hospital 20, the magnetic resonance apparatus 31 in a hospital 30, and the magnetic resonance apparatus 41 in a hospital 40.

In the case of the present exemplary embodiment, the manufacturer 50 would like a systematic judgement of the quality of the globally installed magnetic resonance apparatuses 11, 21, 31 and 41 that are therefore in operation, in order to detect in good time, in particular, systematic quality problems such as modules of insufficient quality owing to defective supply of components, design problems such as unfavorably designed mechanical components, or modules in the magnetic resonance apparatuses 11, 21, 31 and 41 developed in an underdimensioned fashion. For this purpose, computers 12, 22, 32 and 42 in the magnetic resonance apparatuses 11, 21, 31 and 41 transmit to a database 51 of the manufacturer 50 data acquired after regular inspections of the magnetic resonance apparatuses 11, 21, 31 and 41 during the inspections.

The computers 12, 22, 32 and 42 in the magnetic resonance apparatuses 11, 21, 31 and 41 are connected in the case of the present exemplary embodiment to the Internet and transmit the data acquired during the regular inspection automatically to the database 51, likewise connected to the Internet, of the manufacturer 50. A regular inspection is, inter alia, a regular maintenance or a regular quality measurement of one of the magnetic resonance apparatuses 11, 21, 31 and 41.

In the case of the present exemplary embodiment, the magnetic resonance apparatus 11 is inspected by a service technician 13 of the manufacturer 50 in the course of an annual, that is to say regularly conducted, maintenance, the execution of which is known in general to a person skilled in the art and is therefore not explained in more detail.

In the course of this maintenance, the computer 12 in the magnetic resonance apparatus 11 acquires a multiplicity of data that provide information on possible defects in the magnetic resonance apparatus 11. These data comprise, for example, information on defective modules in the magnetic resonance apparatus 11.

The computer 12 automatically transmits these data to the database 51 of the manufacturer 50 after the maintenance. Similar regular maintenance cycles are carried out in the case of the remaining magnetic resonance apparatuses 21, 31 and 41, the computers 22, 32 and 42 in the magnetic resonance apparatuses 21, 31 and 41 likewise transmitting data acquired during the inspections automatically to the database 51.

A regular inspection of the magnetic resonance apparatuses 11, 21, 31 and 41 in global operation is also, for example, one of the measurements that are carried out regularly, inter alia, of the magnet system or RF system of the magnetic resonance apparatuses 11, 21, 31 and 41. These quality measurements are carried out regularly, for example on a weekly basis, and automatically by the computers 12, 22, 32 and 42 in the magnetic resonance apparatuses 11, 21, 31 and 41, in order to ensure no variation in the quality of images produced using the magnetic resonance apparatuses 11, 21, 31 and 41. These quality measurements are familiar to a person skilled in the art in the field of magnetic resonance apparatuses and will therefore likewise not be explained in more detail.

The data acquired by the computers 12, 22, 32 and 42 during the quality measurements are likewise transmitted to the database 51 of the manufacturer 50.

Figure 2:
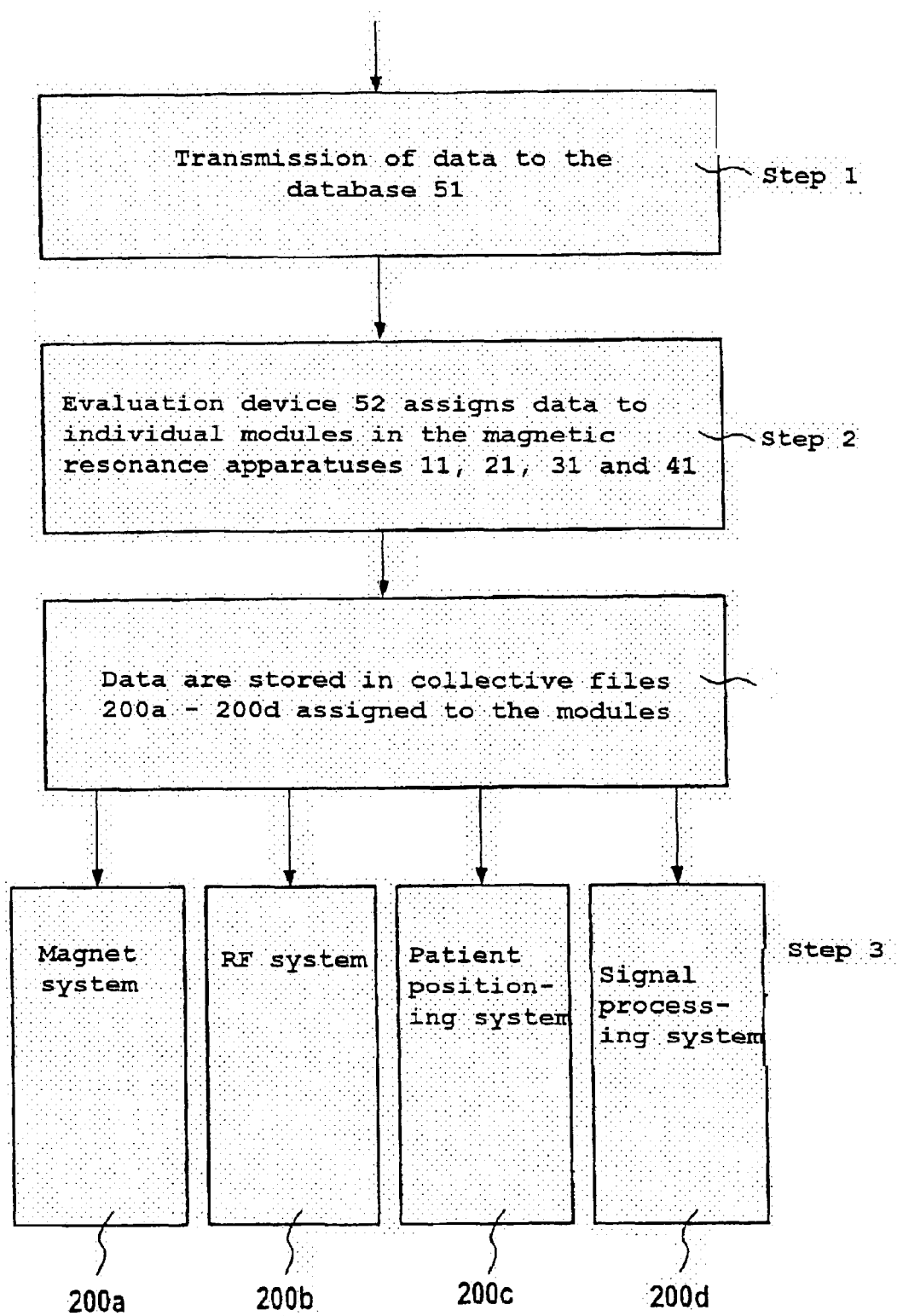
FIG. 2 shows a chart illustrating an evaluation of data transmitted from the magnetic resonance apparatuses.

The database 51 is, moreover, assigned an evaluation device 52 that automatically evaluates the data transmitted to the database 51 by assigning the data transmitted to the database 51 to individual modules in the magnetic resonance apparatuses 11, 21, 31 and 41. The evaluation is explained in more detail schematically with the aid of the chart illustrated in FIG. 2.

In the case of the present exemplary embodiment, the data are classified during acquisition in terms of data types assigned to the individual modules in the magnetic resonance apparatuses 11, 21, 31 and 41. After the data have been transmitted to the database 51 (step 1), they are assigned to the various modules in the magnetic resonance apparatuses 11, 21, 31 and 41 by the evaluation device 52 in the case of the present exemplary embodiment with the aid of their data type (step 2). Thereafter, the data are stored in the database 51 in accordance with their assignment in corresponding collective files 200a to 200d (step 3). In the case of the present exemplary embodiment, one collective file 200a is assigned to a magnet system, one collective file 200b is assigned to an RF system, and one collective file 200c is assigned to a patient positioning system of the magnetic resonance apparatuses 11, 21, 31 and 41, and also a collective file 200d is assigned to a signal processing system for processing images taken by the magnetic resonance apparatuses 11, 21, 31 and 41.

In each of these collective files 200a to 200d, therefore, information from individual modules in a plurality of magnetic resonance apparatuses 11, 21, 31 and 41 of a generic type that are in operation is stored systematically and, in the case of the present exemplary embodiment, can be monitored relatively easily by a quality manager 53 illustrated in FIG. 1. On the basis of the systematic classification of the data transmitted by the magnetic resonance apparatuses 11, 21, 31 and 41 into the collective files 200a to 200d, the quality manager 53 can quickly detect any quality problems that have accumulated and are affecting individual modules, and can therefore identify systematic quality problems in the magnetic resonance apparatuses 11, 21, 31 and 41 that are in operation. Moreover, he can react in a suitable way by, for example, informing a person (not illustrated in FIG. 1) in the development department of the manufacturer 50 of the systematic quality problems in order that, for example, underdimensioned modules can be replaced preventatively by improved modules, in particular including in the case of magnetic resonance apparatuses for which no quality defects have yet occurred. It is thereby possible to reduce unforeseen malfunctions of the magnetic resonance apparatuses 11, 21, 31 and 41, and thus to enhance the satisfaction of the owners of the magnetic resonance apparatuses 11, 21, 31 and 41.

The data for the systematic assessment of the quality of the magnetic resonance apparatuses 11, 21, 31 and 41 do not, however, necessarily need to be determined during maintenance or a quality measurement. It is also possible to determine data during another regular inspection of the magnetic resonance apparatuses 11, 21, 31 and 41. The data also need not be classified during acquisition in terms of data types assigned to modules. The evaluation of the data as described with the aid of the evaluation device 52 is also to be understood only as an example.

The data also need not necessarily be determined with the aid of computers L2, 22, 32 and 42 in the magnetic resonance apparatuses 11, 21, 31 and 41 and transmitted to the database 51. The data can also be stored, for example, on a laptop and transmitted to the database 50 after the inspection.

Transmitting the data via the Internet is also not obligatory for the invention. It is, in particular, also possible to use an Intranet, an Extranet or a telephone network. In the case of the use of the telephone network, the computers 12, 22, 32 and 42 can, for example, be connected to the telephone network using a modem.

The medical appliances need not necessarily be magnetic resonance apparatuses 11, 21, 31 and 41. In particular, the method according to the invention can be used advantageously for systematically assessing computer tomographs, lithotripters, ultrasonic appliances or X-ray machines that are in operation. Other medical appliances can also be used, of course.

The number of inspected medical appliances is also to be understood only as an example. The medical appliances also need not necessarily be globally installed.

The database 51 likewise need not necessarily be assigned to the manufacturer 50 of the medical appliances. In particular, the database 51 can be assigned to a sales organization or a marketing organization for the medical appliances.

What is claimed is:

1. A method for systematically assessing the quality of medical appliances of a generic type that are in operation, having the following method steps:
    a) for medical appliances comprising plural operational modules, acquiring data that are generated during a regular inspection of the medical appliances (11, 21, 31, 41) at the site of the medical appliances (11, 21, 31, 41),
    b) transmitting the data to a central database (51),
    c) assigning the transmitted data to modules in the medical appliances (11, 21, 31, 41), and
    d) storing the data in collective files (200a to 200d), assigned to the modules in the medical appliances (11, 21, 31, 41), of the central database (51) on the basis of the assignment to the modules in the medical appliances (11, 21, 31, 41),
    wherein each collective file corresponds to a different one of the operational modules.

2. The method for systematically assessing the quality of medical appliances that are in operation as claimed in claim 1, in which the regular inspection is a regular maintenance, a regular calibration measurement and/or a regular quality measurement.

3. The method for systematically assessing the quality of medical appliances that are in operation as claimed in claim 1, in which the data are acquired by computers (12, 22, 32, 42) in the medical appliances (11, 21, 31, 41).

4. The method for systematically assessing the quality of medical appliances that are in operation as claimed in claim 1, in which the data are transmitted with the aid of an information transmission network to which the medical appliances (11, 21, 31, 41) and the database (12, 22, 32, 42) can be connected.

5. The method for systematically assessing the quality of medical appliances that are in operation as claimed in claim 4, in which the information network is a telephone network, the Internet, an Intranet or an Extranet.

6. The method for systematically assessing the quality of medical appliances that are in operation as claimed in claim 3, in which the computers (12, 22, 32, 42) transmit the data to the database automatically.

7. The method for systematically assessing the quality of medical appliances that are in operation as claimed in claim 1, in which the medical appliances are magnetic resonance apparatuses (11, 21, 31, 41), computer tomographs, lithotripters, ultrasonic appliances or X-ray machines.

8. The method for systematically assessing the quality of medical appliances that are in operation as claimed in claim 1, in which the database (51) is assigned to a manufacturer (50), a marketing organization or a sales organization of the medical appliances (11, 21, 31, 41).

9. A method for collecting and analyzing the operation of a plurality of like medical equipment, comprising the steps of:
    a) collecting data at each of a plurality of like medical equipment, the data relating to the operations of plural subsystems of the medical equipment;
    b) transmitting the collected data to a central database over a communications network;
    c) at the central database, separating the transmitted data into data sets associated with each of the operations of the plural subsystems;
    d) for each operation of the plural subsystems, storing the separated transmitted data corresponding to that operation into a corresponding collective file so that data for that operation for the plural medical equipment are collected into the same collective file; and
    e) assessing the operation of the plurality of medical equipment for plural of the operations by examining the data collected in the corresponding plural collective files,
    wherein each collective file corresponds to a different one of the subsystems of the medical equipment.

10. The method of claim 9, wherein step a) data collection is taken at regular maintenance inspections.

11. The method of claim 9, wherein step a) data collection is taken at a regular calibration measurement.

12. The method of claim 9, wherein ones of the plural medical equipment are located at plural hospitals.

13. The method of claim 9, wherein,
    the plural medical equipment are magnetic resonance apparatuses, and
    the collective files in one collective file assigned to a magnet system, one collective file assigned to an RF system, and one collective file assigned to a patient positioning system of the magnetic resonance apparatuses.

* * * * *